US007097845B2

(12) United States Patent
Petersen

(10) Patent No.: US 7,097,845 B2
(45) Date of Patent: Aug. 29, 2006

(54) COMBINATIONS OF ANTIGEN AND MUCOSAL BINDING COMPONENT FOR INDUCING SPECIFIC IMMUNOLOGICAL TOLERANCE

(75) Inventor: Jacob Sten Petersen, 5501 17$^{th}$ Ave. NE., Seattle, WA (US) 98105

(73) Assignee: Jacob Sten Petersen (DK)

( * ) Notice: Subject to any disclaimer, the term of this patent is extended or adjusted under 35 U.S.C. 154(b) by 0 days.

(21) Appl. No.: 09/064,682

(22) Filed: Apr. 22, 1998

(65) Prior Publication Data

US 2002/0119159 A1 Aug. 29, 2002

Related U.S. Application Data

(60) Provisional application No. 60/044,184, filed on Apr. 23, 1997, and provisional application No. 60/044,182, filed on Apr. 23, 1997.

(51) Int. Cl.
*A61K 39/02* (2006.01)
*A61K 39/108* (2006.01)
*A61K 39/35* (2006.01)

(52) U.S. Cl. .................. 424/236.1; 424/241.1; 424/275.1; 424/282.1; 424/810; 514/885; 530/868

(58) Field of Classification Search .............. 424/236.1, 424/241.1, 275.1, 282.1, 810; 514/885; 530/868
See application file for complete search history.

(56) References Cited

U.S. PATENT DOCUMENTS

| 4,666,837 A | | 5/1987 | Harford et al. | |
| 5,399,347 A | | 3/1995 | Trentham et al. | |
| 5,681,571 A | * | 10/1997 | Holmgren et al. | ....... 424/236.1 |

FOREIGN PATENT DOCUMENTS

| EP | 0 474 453 A2 | 3/1992 |
| EP | 666 080 A1 | 8/1995 |
| JP | 2-235823 | 9/1990 |
| JP | 3-109328 | 5/1991 |
| WO | WO 91/08760 | 6/1991 |
| WO | WO 91/12816 | 9/1991 |
| WO | WO 92/07581 | 5/1992 |
| WO | WO 93/16724 | 9/1993 |
| WO | WO 94/07516 | 4/1994 |
| WO | WO 94/27634 | 12/1994 |
| WO | WO 95/10301 | 4/1995 |
| WO | WO 96/17620 | 6/1996 |
| WO | WO 96/21458 | 7/1996 |
| WO | WO 96/39176 | 12/1996 |

OTHER PUBLICATIONS

Elson, Charles O. et al. (1984). "*Generalized Systemic and Mucosal Immuniry in Mice after Mucosal stimulation with Cholera Toxin,*" Chemical Immunology 132(6): 2736–2741.

Liu, L.M. et al. (1998). "*T–Cell Response to Orally Administered Antigens and Its Role in the Treatment of Autoimmune Diseases,*" Chemical Immunology 71: 139–160.

McKenzie, Sara J. et al. (1984). "*Cholera Toxin B Subunit as a Carrier Protein to Stimulate a Mucosal Immune Response,*" 153(4): 1818–1824.

Strobel, Stephan et al. (1998). "*Immune Responses to Dietary Antigens: Oral Tolerance,*" 19(4).

Yankelevich, B. et al., "Prevention of Acute Graft–Versus–Host Disease by Treatment with a Novel Immunosuppressant" *J. Immunol.* 154:3611–3617 (1995).

Chen et al., "Regulatory T cell clones induced by oral tolerance: Suppresion of autoimmune encephalomyelitis" *Science* 265:1237–1240 (1994).

Elson, "Cholera toxin and its subunits as potential oral adjuvants" *Curr. Top. Microbial. Immunol.* 146:29–33 (1989).

Frey et al., "Role of the glycocalyx in regualting access of microparticles to apical plasma membranes of intestinal epithelial cells: Implications for microbial attachment and oral vaccine targeting" *J. Exp. Med.* 184:1045–1059 (1996).

McKenzie et al., "Cholera toxin B subunit as a carrier protein to stimulate a mucosal immune response" *J. Immunol.* 139:1818–1824 (1984).

Nedrud et al., "combined oral/nasal immunization protects mice from sedai virus infection" *J. Immunol.* 139:3484–3492 (1987).

Sun et al., "Cholera Toxin B subunit: An efficient transmucosal carrier–delivery system for induction of peripheral immunological tolerance" *Proc. Natl. Acad. Sci. USA* 91:10795–10799 (1994).

Sun et al., "Treatmnet of experimental autoimmune encephalomyelitis by feeding myelin basic protein conjugated to cholera toxin B subunit" *Proc. Natl. Acad. Sci. USA* 93:7196–7201 (1996).

Thompson et al., "suppression of collagen induced arthritis by oral administration of type II collagen: Changes in immune and arthritic responses mediated by active peripheral suppression" *Autoimmunity* 16:189–199 (1993).

(Continued)

*Primary Examiner*—Rodney P Swartz
(74) *Attorney, Agent, or Firm*—Morrison & Foerster, LLP

(57) ABSTRACT

This invention provides combinations of a tolerance-inducing antigen such as insulin and a mucosal binding component that preferably binds ganglioside GM1. The components are present in a non-covalent arrangement. When administered to a mucosal surface, the combinations are effective in inducing specific immunological tolerance at a 10-fold lower dose than antigen alone. Tolerance is sustained for a number of weeks without the necessity of booster administrations. The compositions and procedures of this invention are of benefit for the prevention or amelioration of conditions attributable to an unwanted immunological response.

17 Claims, No Drawings

OTHER PUBLICATIONS

Wang et al., "T cell reactivity to acetylcholine receptor in rats orally tolerized against experimental autoimmune myastheina gravis" *Cell Immunol.* *152*:394–404 (1993).

Weiner et al., "Oral tolerance: Immune mechanisms and treatment of autoimmune diseases" *Immunology Today* *18*:335–343 (1997).

Whitacre et al., "Oral tolerance in experimental autoimmune encephalomyelitis III. Evidence for clonal anergy" *J. Immunol.* *147*:2155–2163 (1991).

Zhang et al., "Suppression of diabetes in nonobese diaetic mice ty odminstration of porcine insulin" *Proc. Natl. Acad. Sci. USA* *88*:10252–10256 (1991).

* cited by examiner

US 7,097,845 B2

COMBINATIONS OF ANTIGEN AND MUCOSAL BINDING COMPONENT FOR INDUCING SPECIFIC IMMUNOLOGICAL TOLERANCE

RELATED APPLICATIONS

This application claims the priority benefit of U.S. Provisional Application 60/044,184, filed Apr. 23, 1997, pending; and U.S. Provisional Application 60/044,182, filed Apr. 23, 1997, pending. The aforelisted patent applications are hereby incorporated herein by reference in their entirety.

TECHNICAL FIELD

This invention relates generally to the field of oral tolerization. More specifically, it provides products and methods for treating diabetes and other conditions involving an unwanted immune response by specifically inhibiting the immunological reactivity that contributes to the pathological effects of the condition.

BACKGROUND

There is increasing awareness that many human maladies relate to a malalignment of the immune system with the needs of the host. Failure to eliminate a pathogenic microorganism often stems from immune hyporesponsiveness or inadequate effector action. On the other hand, tissue destruction in the absence of an invading organism often stems from immune over-responsiveness to an autoantigen. Small-molecule drugs have been developed which are powerful non-specific immune enhancers or depressants. But they are blunt instruments for what is really required—a focused modulation of immune reactivity against a few selected target molecules.

One of the challenges in addressing this question is understanding the difference in the underlying mechanisms for immunogenicity and immunotolerance: respectively, the upward and downward modulation of immunological reactivity. In certain contexts, both types of modulation involve an inducing antigen in a complex interaction with antigen presenting cells and T cells.

The mucosal immune system is more biased towards non-responsiveness and tolerization of a foreign antigen than the systemic immune system. Clearly, reaction against all the foreign substances in the diet would deplete the resources of the system. The mechanisms that dampen responsiveness include clearance of food antigens from the portal circulation by Kuppfer cells, and sampling of antigen through M cells of Peyer's patches and mature enterocytes for presentation to the immune system in a tolerogenic context. Lymphocytes and other cells participating in the mucosal immune system secrete a different spectrum of cytokines and bear a different spectrum of surface markers from their counterparts in the systemic immune system.

The mucosal immune system is common to different mucosal sites, including the bronchus, breast and bowel (Bienenstock et al., *Adv. Exp. Med. Biol.* 107:53, 1978). In contrast, the mucosal and systemic immune systems are partitioned from each other. The tolerogenic response in the gut involves regulatory TGF-β, IL-4, and IFN-γ secreting T cells (Leonilda et al., *Cell. Immunol.* 157:439, 1994; Zeng-Yu et al., *Cellular Immunol.* 157:353, 1994). Cells in the efferent vessel of mesenteric lymph nodes preferentially home back to the mucosa, whereas cells in the efferent vessel of peripheral nodes preferentially home back to the periphery. Nevertheless, there is enough cross-over between the systems that a response invoked in the gut is shared into the systemic compartment. Thus, the Sabin polio vaccine induces protection against polio both at the mucosal surface and in the circulation. Tolerance induced against certain antigens presented in the gut can lead to a systemic non-responsiveness against those antigens.

Efforts have been made to take advantage of the mucosal bias towards tolerance as a mode of therapy for specific immunological down-regulation. For reviews of the area, see Thompson et al. (*Immunol. Today* 11:197, 1990); Weiner (*Proc. Natl. Acad Sci USA* 91:10762, 1994); MacDonald (*Curr. Biol.* 4:178, 1994); and Weiner et al. (*Annu. Rev. Immunol.* 12:809, 1994). Generally, the approach has been to intubate an antigen into the small intestine of animals with an aberrant immune response, in an effort to lower the responsiveness and thereby improve the condition.

International patent publication WO 91/12816 and EP Patent Application EP 666 080 A1 recites treatment of autoimmune diseases by oral administration of autoantigens. The autoantigen is specific for an autoimmune disease and is orally or enterally administered for eliciting suppressor T cells that recognize the autoantigen. International patent publication WO 91/08760 recites treatment of autoimmune diseases by aerosol administration of autoantigen.

International patent publication WO 96/39176 recites the use of oral administration of antigen to suppress both $T_{H1}$ and $T_{H2}$ immune responses and suppress antibody production. In working examples, the antigen was fed ad libitum in the drinking water, and dependent claims recite at least 6 doses per day or sustained release.

International patent publication WO 93/16724 recites treatment of autoimmune disease by administering a bystander antigen rather than an autoantigen associated directly with the disease. The bystander antigen elicits release of TGF-β at a locus within the body of mammals, wherein T cells contributing to autoimmune response are found to suppress the T-cells contributing to the disease. International patent publication WO 94/27634 recites cryptic peptides for use in inducing immunologic tolerance. Cryptic epitopes are those determinants in a protein antigen which, due to processing and presentation of the native protein antigen, are not normally revealed to the immune system.

A number of patent disclosures and academic articles recite treatment of particular conditions by tolerizing through a mucosal route. U.S. Pat. No. 5,399,347 and Thompson et al. (*Autoimmunity* 16:189, 1993) recite methods of treating rheumatoid arthritis with whole Type II collagen administered orally. International patent publication WO 94/27634 and Vrabec et al. (*Autoimmunity* 12:175, 1992) recite treating autoimmune uveoretinitis by orally administering S antigen. Chen et al. (*Science* 265:1237, 1994) and Whitachre et al. (*J. Immunol.* 147:2155, 1991) recite suppression of autoimmune encephalomyelitis by oral administration of myelin basic protein (MBP). Wang et al. (*Cell. Immunol.* 152:394, 1993) recite oral administration of acetylcholine receptor to orally tolerize against experimental autoimmune myasthenia gravis.

International patent publication WO 94/27634 recites treating type I diabetes by oral administration of insulin. For other experiments in non-obese diabetic (NOD) mice, see Ramiya et al. (*Diabetes* 44:164A, 1995) and Zhang et al. (*Proc. Natl. Acad. Sci. USA* 88:10252, 1991). In a virus-induced antigen-specific diabetic model, oral treatment with insulin started 1 week before or 10 days after the initiating viral challenge prevented appearance of hyperglycemia in >50% of the mice. Oral administration was believed not to affect the generation of anti-beta cell cytotoxic T lymphocytes nor infiltration into the pancreas, but less beta cells were destroyed. The majority of lymphocytes in the islets of successfully treated insulin-treated mice produced IL-4, IL-10, and TGF-β, whereas lymphocytes from symptomatic mice produced mainly γ-IFN.

International patent publication WO 92/07581 recites methods and compositions for suppressing allograft rejection in mammals. The graft recipient is administered by oral or aerosol administration of an agent selected from the group consisting of spleen cells, cultured cells, or extracts derived from the donor or MHC antigens.

The aforementioned disclosures typically indicate that the tolerizing antigen must be administered frequently, up to several times a day, or at a dose of over 1 mg/mouse. In order to maintain tolerance, it is generally necessary to administer the antigen on an ongoing basis.

Cholera toxin is a prototype bacterial enterotoxin released by *Vibrio cholerae,* and induces active electrolyte and water secretion from the intestinal epithelium. It is a protein built from a single A subunit of 28,000 mol. wt. and five B subunits of 11,600 mol wit. The B subunits are aggregated in a ring by tight noncovalent bonds; the A subunit is attached to and probably partly inserted in the B pentamer ring through weaker noncovalent interactions. The B subunits are responsible for cell binding, and the A subunit has toxic activity involving modifying the G proteins of the cyclic AMP pathway. The binding activity of the B subunit is towards the ganglioside GM1, which is present on the mucosal surface.

There is an extensive literature regarding the ability of cholera toxin to work as an adjuvant in mucosal vaccines, increasing the level of the immune response against the antigen it is mixed with. See, for example, Elson, *Curr. Top. Microbiol. Immunol.* 146, 1989; Nedrud et al., *J. Immunol.* 139:3484, 3492, 1987; and McKenzie et al., *J. Immunol.* 133:1818, 1984.

More recently, the CTB subunit coupled to certain antigens have been indicated as having a tolerance-inducing effect when administered to a mucosal surface.

International patent publication WO 95/10301 recites an immunological tolerance-inducing agent comprising a mucosa binding molecule coupled to a specific tolerogen. Exemplary mucosa-binding structures were CTB and subunit of heat-labile enterotoxin of *E. coli.*

Sun et al. (*Proc. Natl. Acad. Sci. USA* 93, 7196, 1996) recites CTB as an efficient transmucosal carrier-delivery system. Red blood cells were modified by covalently coupling with GM1, which was then attached with the CTB. HGG was modified by covalently coupling directly to CTB. A single oral administration of a soluble or particulate antigen coupled to CTB enhanced tolerance. Sun et al. (*Proc. Natl. Acad. Sci. USA* 93, 7196, 1996) recites treatment of experimental autoimmune encephalomyelitis by feeding myelin basic protein covalently conjugated to CTB.

International patent publication WO 96/21458 recites collagen-based methods and formulations for treatment of immune system-mediated diseases like autoimmune liver disease, Crohns disease, Goodpasture's syndrome, psoriasis, localized sclerosis, the various manifestations of arthritis, and various localized degradative inflammatory or fibrotic conditions. The compound is administrered linked to a mucosa binding molecule such as CTB.

In the experiments of these publications, the effective ingredient was assembled by conjugating with antigen with either the CTB directly, or with a linker group.

SUMMARY OF THE INVENTION

The combinations of the present invention contain an inducing antigen and a mucosal binding component which are not covalently attached to each other, and are effective in inducing specific immunological tolerance when administered to a mucosal surface. These compositions are an improvement over prior art compositions of antigen alone, because they can induce tolerance at a 10-fold lower dose and lead to a more sustained response. They are more convenient in comparison with covalently linked complexes in their ease and economy of preparation.

An embodiment of the invention is a method of inducing sustained immunological tolerance in an individual to a target antigen, comprising administering to a mucosal surface of the individual a composition comprising an effective combination of an inducing antigen and a mucosal binding component in an unconjugated form. The inducing antigen may be the target antigen against which tolerization is desired, or a bystander for the target antigen. Inducing antigens may be autoantigens (including but not limited to insulin peptides, collagen peptides, and MBP peptides), alloantigens (including, but not limited to, HLA class I and II), xenoantigens, or allergens. Mucosal binding components typically have GM1 binding activity, and are exemplified by choleratoxin B and LTB.

Another embodiment of the invention is a method of treating an autoimmune disease or allergic condition in an individual, comprising inducing sustained immunological tolerance as described above.

Another embodiment of the invention is a pharmaceutical composition comprising an effective combination of a mucosal binding component and an inducing antigen in an unconjugated form. Preferred compositions for treating diabetes contain insulin as the inducing antigen, and metal cations such as zinc. Also embodied is a method for preparing such pharmaceutical compositions, comprising combining the components at the weight ratio of the effective combination.

Further embodiments relate to inducing tolerance in the context of tissue transplantation. One such embodiment is a method of decreasing the risk of rejection in a recipient of a tissue graft transplanted from a donor, comprising inducing immunological tolerance in the recipient to cells of the donor by administering to a mucosal surface of the recipient a composition comprising an effective combination of an inducing antigen and a mucosal binding component in an unconjugated form. Both xenografts and allografts are included. Another such embodiment is a method of decreasing the risk of graft-versus-host disease in a recipient of a tissue graft transplanted from a donor, comprising inducing immunological tolerance in the donor to cells of the recipient by administering to a mucosal surface of the donor a composition comprising an effective combination of an inducing antigen and a mucosal binding component in an unconjugated form. The inducing antigen may be, for example, a single HLA antigen or an HLA antigen cocktail, or a cell or cell derivative from one or more individuals.

Also embodied is an improved method of transplanting a tissue graft from a donor into a recipient, the improvement comprising decreasing the risk of rejection of the tissue graft or the risk of graft-versus-host disease according to this invention.

Yet another embodiment is a pharmaceutical composition for decreasing the risk of rejection in a recipient of a tissue graft transplanted from a donor, or the risk of a graft versus host disease, comprising an effective combination of an inducing antigen or plurality of antigens in the form of purified molecules or cell derivatives, and a mucosal binding component in an unconjugated form. Also embodied are methods for producing such compositions comprising combining the components at the weight ratio of the effective combination.

Further embodiments relate to kits for use in decreasing the risk of rejection in a recipient of a tissue graft transplanted from a donor or the risk of a graft-versus-host disease, comprising a mucosal binding component for mixing with a cell or cell extract to produce an effective combination. The kit may optionally include an inducing antigen or panel of such antigens. Also embodied is a method for producing such kits, comprising packaging in kit form a sufficient amount of the mucosal binding component to permit a user of the kit to prepare the effective combination.

DETAILED DESCRIPTION

It is an object of this invention to provide a system for inducing specific immunological tolerance, using compositions that are easily assembled and administered.

The compositions minimally comprise the following two components in an effective combination:

a mucosal binding component, such as choleratoxin B subunit (CTB)

an inducing antigen such as insulin, which is either the target for which tolerance is desired, or a bystander for the target.

The inducing antigen can be mixed with the mucosal binding component before administration, they can be administered separately, or the antigen may already be present at the mucosal surface. When given together, the mucosal binding component and the inducing antigen are unconjugated, which means that they are not covalently bound to each other, either directly or through an intermediate linker.

Application of the compositions to a mucosal surface results in specific immunological tolerance against the target antigen. Typically, tolerance is induced by treatment with a plurality of administrations, which can be given approximately every two weeks. The immunological tolerance that results is typically sustained, which means that immunological or clinical indicators of tolerance are observable in a proportion of subjects receiving the treatment for a sustained period of many weeks, at least 3 weeks, typically at least about 5 weeks, and preferably at least about 10 or even 15 weeks after the last of the initiating administrations. Additional booster administrations can be given during or following this period to promote the level of tolerance. While not intending to be bound by theory, it appears that sustained tolerance involves at least in part an active immunosuppression of immune B or T cells specific for the target antigen.

Results underlying the invention were discovered during development of covalent conjugates between insulin and CTB, and their subsequent testing as oral tolerogens in the NOD mouse model for diabetes. Control groups of mice included those treated with insulin or CTB alone, or a non-covalent mixture of the two. A small amount of tolerance at high levels of insulin alone was expected in view of previous descriptions of the effect of mucosal administration of insulin. Some of the insulin-CTB covalent conjugates were much more potent at inducing tolerance. It turned out that the non-covalent mixture of insulin and CTB was very potent at inducing tolerance, much more than insulin alone.

Example 1 describes a follow-up experiment in which the nature of the response to non-covalent combinations was further characterized.

The results of these experiments demonstrate that non-covalent combinations have the following unexpected properties:

The combinations induced tolerance when orally administered at concentrations about 10 times lower than the amount needed to induce tolerance using insulin alone.

Unlike the effect of insulin alone, the tolerance induced by the non-covalent combination was sustained for a longer period of time. The treatment was able to forestall the onset of diabetic symptoms in a substantial proportion of NOD mice for at least 17 weeks after the beginning of treatment.

The mechanism whereby the mucosal binding component potentiates the tolerogenic potential of the antigen is not fully elucidated. An understanding of the mechanism is not required to practice the invention nor is any limitation intended by the following explanations. In one possible mechanism, the mucosal binding component may facilitate the ability of the antigen to penetrate the mucosal surface and accumulate near antigen presenting or regulatory cells participating in specific tolerance. Alternatively or in addition, when the combination is given in a number of repeat doses, the mucosal binding component may prime mucosal immunity, which results in a rapid effector response to subsequent doses of the mixture. This in turn may contribute cytokines or other soluble factors that increase the receptivity of regulatory T cells to a lower amount of the antigen in the mixture. In a third explanation, the potentiating effect of CTB may be mediated by crosslinking GM1 on lymphocytes or antigen-presenting cells. Example 2 shows that CTB given to cell cultures before antigen apparently potentiates presentation and increases $T_{H1}$ cells (secreting IL-2 and IFN-γ) and $T_{H2}$ (secreting IL-4). CTB crosslinking of GM1 on cells of the mucosal immune system may heighten a specific activation of suppressor cells.

While the antigen and the mucosal binding component may optionally associate in a non-covalent fashion, this is not believed to be necessary to obtain the desired effect. The invention includes compositions where some or all of the components are non-covalently associated with each other when in aqueous solution, and compositions where the components are not associated.

This invention provides certain advantages in inducing immunological tolerance that will be of interest for treating unwanted immunological responses. Because the mucosal binding component potentiates the ability of the inducing antigen to induce tolerance, a considerably smaller dose of antigen can be given. The sustained nature of the response also means that booster doses can be given less often. Because the composition is assembled by merely mixing the components, preparation is rapid. The ease of assembling the composition means that testing of new components, combinations and proportions is facilitated, and that the commercial production of proven compositions can be done at low cost. Very complex mixtures can also be obtained, whereby the mucosal binding component potentiates tolerization to antigens that may be present in an antigen cocktail, a cell extract, or a cell lysate.

Additionally, the present invention provides the advantage of manipulating the immune system to create new therapeutic strategies. It is contemplated that immunological tolerance can be stimulated towards target antigens of an undesired hypersensitivity response to foreign antigen. Target antigens include foods, food additives, pollen, fungal spores, dusts or animal dander. Exposure may occur through the gastrointestinal tract, by inhalation, or through skin contact. A mucosal binding component such as CTB is administered prior to, concurrent with, or shortly following the source of the offending antigen, or else mixed directly with a sample of the antigen before administration. When administered separately, the components are given within a period wherein the mucosal binding component can promote tolerance against the inducing antigen, and preferably as close together as possible.

The invention further provides methods of inducing immunological tolerance to target antigens present on the mucosal surface. Of particular interest are target antigens preferentially associated with mucosal disorders, exemplified by inflammatory bowel disease, irritable bowel syndrome, ulcerative colitis, Celiac disease and Crohn's disease. A mucosal binding component such as CTB is administered to a patient suffering from a mucosal disorder to create an environment conducive to the induction of tolerance in the presence of the endogenous target antigens associated with the mucosal disorder. Certain target antigens will already be present on the mucosal surface, and the level or nature of expression may be altered by the disease condition. The administered CTB creates an effective combination in situ to generate specific tolerance.

Specific tolerance is desirable for ameliorating, limiting, or postponing the onset of an unwanted immune response in a subject. Accordingly, the methods and compositions of this invention are of considerable interest in the treatment of a number of human diseases having an etiology involving an unwanted immune response.

Definitions and General Techniques

A method or composition is referred to herein as invoking "immunological tolerance" if it has at least one of these effects on a proportion of treated subjects in comparison with untreated subjects: a) a decreased level of a specific immunological response (thought to be mediated at least in part by antigen-specific effector T lymphocytes, B lymphocytes, antibody, or their equivalents); b) a delay in the onset or progression of a specific immunological response; or c) a reduced risk of the onset or progression of a specific immunological response. "Specific" immunological tolerance occurs when immunological tolerance is preferentially invoked against certain antigens in comparison with others.

"Active" immunological tolerance refers to a state in which the tolerance effect(s) are the result of an ongoing biological process: for example, down-regulation of specific effector cells by suppressor cells. Active tolerance can be demonstrated by cell mixing or cell transfer experiments. The following two examples of experimental results (conducted with appropriate controls) are evidence of active immunological tolerance: a) when leukocytes from a tolerized animal are mixed with specific effector cells from a second animal and the activity of the effector cells is diminished; b) when leukocytes from a tolerized animal are transferred to a second animal having an autoimmune disease, and features of the disease are reduced.

"Sustained tolerance" is tolerance that measurably persists for at least 3 weeks.

The terms "polypeptide", "peptide" and "protein" are used interchangeably herein to refer to polymers of amino acids of any length. The term "polynucleotide" refers to a polymeric form of nucleotides of any length, either deoxyribonucleotides or ribonucleotides, or analogs thereof, and includes plasmids and vectors. When sequences are compared between proteins or between polynucleotides, occasional gaps are permitted that clearly are required to align substantial regions of homology, except where the residues in a linear sequence are defined as "consecutive".

As used in this disclosure, a "target antigen" is an antigen for which immune tolerance is desired. Typically, the target antigen will also be the target of an unwanted immunological response (already underway or for which the subject is at risk), and an object will be to decrease, delay, or reduce the risk of the response.

An "inducing antigen" is an antigen included in the combinations of this invention for invoking tolerance. It may be the target antigen, or a fragment or derivative thereof. Alternatively, it can be a bystander antigen.

A "bystander antigen" is an antigen which is antigenically distinct from the target antigen but can substitute for the target antigen in invoking specific immunological tolerance. Usually, a bystander antigen is expressed in the same tissue in the vicinity of the target antigen. The possible mechanisms by which bystander antigens play their role are elaborated elsewhere in this disclosure.

A "dietary antigen" is any antigen that can be encountered by dietary consumption, including antigens present in food components and food additives. A "mucosal antigen" is an antigen expressed at a mucosal surface, either constitutively or by induction, for example in the course of inflammation or disease. An "allergen" is an antigen which can generate a Type I hypersensitivity reaction in a presensitized individual.

Molecules are referred to herein as being "conjugated" or "linked" if they are covalently bonded to each other, either directly, or through one or more linker molecules. The terms confer no other limitation as to the nature of the linkage or the product formed. Thus, for example, disulfide-bonding amino acid chains are conjugated; the first half of a polypeptide chain is conjugated to the second half. "Unconjugated" molecules are not conjugated or linked to each other.

Two molecules in a preparation are referred to herein as being "associated" if, when the preparation is dissolved or diluted in 100 mL of isotonic buffer at pH~7, at least 50% of the molecule not in excess is associated into a non-covalent heterodimer or heteropolymer of both molecules. In certain embodiments, any association between the molecules has an association constant $<10^{10}$ $M^{-1}$, preferably $<10^8$ $M^{-1}$. Two "unassociated" molecules are neither conjugated nor associated.

"Treatment" refers to clinical intervention in an attempt to alter the natural course of the individual being treated, and may be performed either for prophylaxis or during the course of clinical pathology. Desirable effects include preventing occurrence or recurrence of disease, alleviation of symptoms, diminishment of any direct or indirect pathological consequences of the disease, lowering the rate of disease progression, and so on, as may be measured by clinical features and generally accepted biochemical, immunological, or histopathological features of the condition. The pathology associated with a disease condition is anything that compromises the well-being, normal physiology, or quality of life of the affected individual.

An individual or subject treated using the compositions and methods of this invention will be a vertebrate, particularly a mammal (including farm animals, sport animals, and pets), and frequently a human.

An "effective combination" of components in a preparation used for treatment comprises an amount of each of the components which, in combination, attains the desired effect. The effect may be achieved in one or a series of administrations.

An "effective proportion" of components in a component mixture has the same proportion of components (on a wt/wt basis) as an effective combination. The mixture can therefore be divided, dissolved, or diluted to produce a composition for effective administration.

The practice of the present invention will employ, unless otherwise indicated, conventional techniques of molecular biology, microbiology, recombinant DNA, and immunology, which are within the skill of the art. See, for example, "Molecular Cloning: A Laboratory Manual", Second Edition (Sambrook, Fritsch & Maniatis, 1989), "Animal Cell Culture" (R. I. Freshney, ed., 1987); the series "Methods in Enzymology" (Academic Press, Inc.); "Handbook of Experimental Immunology" (D. M. Weir & C. C. Blackwell, eds.), "Gene Transfer Vectors for Mammalian Cells" (J. M. Miller & M. P. Calos, eds., 1987), "Current Protocols in Molecular Biology" (F. M. Ausubel et al., eds., 1987); and "Current Protocols in Immunology" (J. E. Coligan et al., eds., 1991).

Selection and Preparation of the Mucosal Binding Component

A number of mucosal binding components are suitable for use in this invention. The mucosal binding component comprises one or more molecules capable of specifically binding to the mucosal cells of the subject being treated. In some instances, the mucosal binding component has the additional characteristic of penetrating or translocating across the mucosal surface.

Non-limiting examples of mucosa-binding molecules include the following: 1. Bacterial toxins and their binding subunits or fragments; such as cholera toxin and cholera toxin B subunit, E. coli heat-labile enterotoxin and its B subunit, Bordetella pertussis toxin and the subunits S2, S3, S4, and S5 (in any combination), diphtheria toxin and the β toxin fragment, shiga and shiga-like toxins and their B subunits, staphylococcal α-hemolysin, vibrio thermostable direct hemolysin. 2. Bacterial fimbriaie; such as E. coli K88, K99, 987P, F41, CFA/I, CFA/II (CS4, CS5 and CS6), P fimbriae, V. cholerae toxin co-regulated pili (TCP), mannose-sensitive hemagglutinin (MSHA), fucose-sensitive hemagglutinin (FSITH), B. pertussis filamentous hemagglutinin. 3. Viral attachment proteins; such as influenza hemagglutinin, Sendai virus hemagglutinin, HIV gp120. 4. Plant and animal lectins; such as Con A, wheat-germ agglutinin, phytohemagglutinin, abrin, ricin, C-type lectins, lactose-binding (S-type) lectins, selectins, collectins, hemix potatia hemagglutinins. 5. Monoclonal and polyclonal antibodies against mucosal components (especially but not limited to mucosally expressed carbohydrates), along with antibody fragments and derivatives like diabodies and single-chain variable regions with the desired mucosal component binding activity.

This invention also includes mucosal binding components that are based on a molecule of the appropriate specificity but are adapted by fragmentation, residue substitution, labeling, conjugation, and/or fusion with peptides having other functional properties. The adaptation may be performed for any desirable purposes, including but not limited to the elimination of any undesirable property, such as toxicity or immunogenicity; or to enhance any desirable property, such as mucosal binding, mucosal penetration, or stimulation of the tolerogenic arm of the immune response. Mucosal binding activity can be identified by using isolated cells or histological tissues of the intended site of administration in a standard binding assay.

Preferred mucosal binding components of this invention are capable of binding gangliosides expressed in the mucosa, preferably the ganglioside GM1. Candidate mucosal binding components for use with this invention can be tested for activity by an ability to bind to gangliosides using a molecular or cellular binding assay. Embodiments of this invention explicitly referring to a molecule as having ganglioside or GM1 binding activity require no other property to meet the definition of a mucosal binding component.

A number of assays known in the art can be readily adapted to measure GM1 binding activity. One non-limiting example is a plate-binding ELISA for GM1 binding activity with the following format: Microtiter plate wells are coated overnight with 5 μg purified GM1 (available from Sigma Chemical Co., St. Louis Mo.) in 50 mM sodium carbonate pH 9.6, washed 4 times in assay buffer (PBS, 0.1% Tween™ 20), blocked with 1% bovine albumin in assay buffer, and rewashed. Serial dilutions of the candidate mucosal binding protein in assay buffer are incubated in the wells for ~1.5 h, followed by washing. The wells are developed using a primary antibody against the component that binds to GM1 (e.g., goat anti-CTB), a second enzyme-labeled antibody specific for the primary antibody (e.g., peroxidase-conjugated donkey anti-goat immunoglobulin), and the enzyme substrate (e.g., O-phenylenediamine).

Mucosal binding components can be prepared by a number of techniques known in the art, depending on the nature of the molecule. Those molecules originally identified from bacterial, viral, plant or animal sources may be isolated from those sources according to the original description. Short peptides are conveniently prepared by amino acid synthesis. Lectins and certain other mucosal binding proteins are available from biochemical supply companies. Antibodies are raised by immunizing an animal with the isolated mucosal binding target, and then purifying antibody from serum or raising hybridoma antibodies using lymphocytes from the animal. Longer proteins of known sequence can be prepared by synthesizing an encoding sequence or PCR-amplifying an encoding sequence from a natural source or vector, and then expressing the encoding sequence in a suitable bacterial or eukaryotic host.

Exemplary mucosal binding components are the cholera toxin B subunit (CTB), and the E. coli heat-labile enterotoxin B subunit (LTB). Terms such as CTB peptide and LTB peptide as used herein refer not only to the intact subunit, but also to allelic and synthetic variants, fragments, fusion peptides, conjugates, and other derivatives, that contain a region that is homologous (preferably 70% identical, more preferably 80% identical and even more preferably 90% identical at the amino acid level) to at least 10 and preferably 30 consecutive amino acids to the respective molecule for which it is an analog, wherein the homologous region of the derivative has mucosal binding activity, as may be determined in the binding assays described earlier.

To minimize the risk of enhancing an immune response rather than inducing tolerance, CTB used as a mucosal binding component is in most embodiments essentially free of any intact choleratoxin or functional choleratoxin A subunit. This means that <0.1% and preferably <0.01% of the CTB preparation by weight is active A subunit. Recombinantly obtained CTB is a preferred source as being unlikely to have A subunit as a contaminant.

Cholera toxin and CTB are available from Sigma Chemical Co., St. Louis Mo. The DNA encoding sequence for the cholera toxin A and B chain are disclosed in U.S. Pat. No. 4,666,837. For materials and techniques convenient for preparing recombinant CTB, the reader is referred to EP Patent No. 0095426; U.S. Pat. No. 5,268,276; and Sanchez et al., Proc. Natl. Acad. Sci. USA 86:481, 1989. For materials and techniques convenient for preparing recombinant LTB, the reader is referred to International Patent Publication WO 95/10301 and Hirst et al., *Proc. Natl. Acad. Sci USA* 81:7752, 1984. Proteins secreted from bacteria expression systems can be recovered from growth media by adjusting the pH to 4.5, precipitating with hexametaphosphate (final concentration 2.5 g/L), centrifuging at 8000 RPM, dissolving and dialyzing into phosphate-buffered saline, and then clarifying by centrifugation and ultrafiltration. Preparations can be further purified, for example, by gel filtration chromatography.

Selection and Preparation of the Antigen

The practitioner has a number of choices for antigens used in the combinations of this invention. The inducing antigen present in the combination contributes to the specificity of the tolerogenic response that is induced. It may or may not be the same as the target antigen, which is the antigen present or to be placed in the subject being treated which is a target for the unwanted immunological response, and for which tolerance is desired.

An inducing antigen of this invention may be a polypeptide, polynucleotide, carbohydrate, glycolipid, or other molecule isolated from a biological source, or it may be a chemically synthesized small molecule, polymer, or derivative of a biological material, providing it has the ability to induce tolerance according to this description when combined with the mucosal binding component.

In certain embodiments of this invention, the inducing antigen is a single isolated or recombinantly produced molecule. For treating conditions where the target antigen is disseminated to various locations in the host, it is generally necessary that the inducing antigen be identical to or immunologically related to the target antigen. Examples of such antigens are most polynucleotide antigens, and some carbohydrate antigens (such as blood group antigens).

Where the target antigen is preferentially expressed on a particular organ, cell, or tissue type, the practitioner again has the option of using an inducing antigen which is identical with or immunologically related to the target antigen. However, there is also the additional option of using an antigen which is a bystander for the target. This is an antigen which may not be immunologically related to the target antigen, but is preferentially expressed in a tissue where the target antigen is expressed. A working theory as to the effectiveness of bystander suppression is that suppression is an active cell-mediated process that down-regulates the effector arm of the immune response at the target cells. The suppressor cells are specifically stimulated by the inducer antigen at the mucosal surface, and home to a tissue site where the bystander antigen is preferentially expressed. Through an interactive or cytokine-mediated mechanism, the localized suppressor cells then down-regulate effector cells (or inducers of effector cells) in the neighborhood, regardless of what they are reactive against. If the effector cells are specific for a target different from the inducing antigen, then the result is a bystander effect. For further elaboration of the bystander reaction and a list of tolerogenic peptides having this effect, the reader is referred to International Patent Publication WO 93/16724. An implication of bystander theory is that one of ordinary skill need not identify or isolate a particular target antigen against which tolerance is desired in order to practice the present invention. The practitioner need only be able to obtain at least one molecule preferentially expressed at the target site for use as an inducing antigen.

Insulin-dependent diabetes mellitus involves an autoimmune assault on beta cells of the pancreas, which is the site for insulin production. The focus of the assault is generally thought not to be insulin, but another antigen expressed by the beta cells. However, since insulin, glucagon, and amylin are preferentially expressed by beta cells, any of these is suitable as an inducing antigen for this invention. Purified porcine and bovine insulin and recombinant human insulin are commercially available from many sources for the clinical and veterinary management of glucose metabolism: for example, NovoNordisk, Connaught Laboratories, and Eli Lilly & Co. These preparations may be directly implemented in the practice of this invention, or insulin may be produced by recombinant expression. In certain embodiments, the insulin is from the same species as the subject to be tolerized. In other embodiments, the insulin is from a different species as the subject to be tolerized. The precursor form of insulin (comprising an AAK sequence linking the B chain to the A chain), other single-chain forms, and forms containing a signal peptide for secretion may also be used.

In certain embodiments of this invention, the inducing antigen is not in the same form as expressed in the individual being treated, but is a fragment or derivative thereof. Inducing antigens of this invention include peptides based on a molecule of the appropriate specificity but adapted by fragmentation, residue substitution, labeling, conjugation, and/or fusion with peptides having other functional properties. The adaptation may be performed for any desirable purposes, including but not limited to the elimination of any undesirable property, such as toxicity or immunogenicity; or to enhance any desirable property, such as mucosal binding, mucosal penetration, or stimulation of the tolerogenic arm of the immune response. Terms such as insulin peptide, collagen peptide, and myelin basic protein peptide, as used herein, refer not only to the intact subunit, but also to allotypic and synthetic variants, fragments, fusion peptides, conjugates, and other derivatives that contain a region that is homologous (preferably 70% identical, more preferably 80% identical and even more preferably 90% identical at the amino acid level) to at least 10 and preferably 20 consecutive amino acids of the respective molecule for which it is an analog, wherein the homologous region of the derivative shares with the respective parent molecule an ability to induce tolerance to the target antigen.

It is recognized that tolerogenic regions of an inducing antigen are often different from immunodominant epitopes for the stimulation of an antibody response. Tolerogenic regions are generally regions that can be presented in particular cellular interactions involving T cells. Tolerogenic regions may be present and capable of inducing tolerance upon presentation of the intact antigen. Some antigens contain cryptic tolerogenic regions, in that the processing and presentation of the native antigen does not normally trigger tolerance. An elaboration of cryptic antigens and their identification is found in International Patent Publication WO 94/27634.

A dissection of the native molecule into immunostimulatory and tolerogenic regions is warranted either when an immunodominant region overshadows the tolerogenic effect, or where the only tolerogenic regions are cryptic ones, as in many allergens. The mapping and selection of suitable tolerogenic fragments can be performed using one of the functional assays described in the next section. Both the A and B chain of insulin induce tolerance when used alone, although the B chain is somewhat better at induction. Significant fragments of the mature B chain contain residues 1–12, 10–22 or 11–30, but residues 23–30 are less effective on their own.

Insulin analogs can be prepared by methods known in the art, see for example, Marki et al., *Hoppe-Seyler's Z. Physiol.*

Chem. 360:1619–32, 1979; Kitagawa et al., *Biochem.* 23:4444–8, 1984; Schwartz et al., *Biochem.* 17:4550–6, 1978; Nakagawa et al., *J. Biol. Chem.* 266:11502–9, 1991; Schwartz et al., *Int. J. Pept. Prot. Res.* 17:243–55, 1981; Hu et al., *Biochem.* 32:2631–5. 1993; Nakagawa et al., *J. Biol. Chem.* 261:7332–410, 1986; and Riemen et al., *Biochem.* 22:1507–15, 1983.

It is often unnecessary and sometimes less desirable for the inducing antigen to have functional activity outside its ability to act as tolerance inducing agents. For example, where tolerance to insulin or an insulin bystander is desired, the invention includes using metabolically inactive forms of insulin, metabolically inactive insulin fragments and metabolically inactive insulin analogs. Preferred inactive forms do not have the ability to significantly decrease blood sugar levels within about 4 hours of administration, or are not sufficiently active to treat Type I diabetes, when given at an equivalent dose. Metabolically inactive analogs and fragments include those having an activity which is less than 7%, preferably less than 3%, more preferably less than 1% and still more preferably less than 0.1% of the activity exhibited by normal human insulin. Methods of measuring insulin activity include the euglycemic pig clamp assay, intravenous rabbit blood glucose assay, the mouse fat free cell assay, subcutaneous mouse blood glucose assay and receptor binding assays using whole cells or soluble receptors (Anderson et al., *J. Biol. Chem.* 267:133681–6, 1992; Vølund et al., *Diabetic Med.* 8:839–47, 1991; Moody et al., *Horm. Metab. Res.* 6:12–6, 1974; Vølund, *Biometrics* 34:357–65, 1978; Brang et al., *Diabet. Care* 13:923–54, 1990; and Drejer, *Diabet. Met. Rev.* 8:259–86, 1992).

Exemplary metabolically inactive insulin analogs include X28; X38 (ASp$^{B25}$ human insulin); M13; the insulin A chain; the insulin B chain; des(A1–A2) human insulin; des(A1–A3) human insulin; desA21 human insulin; des(B1–B5) human insulin; des(B1–B6) human insulin; des(B23–B30) human insulin; des(B24–B30) human insulin; des(B25–B30) human insulin; Gly$^{42}$ human insulin; Ala$^{42}$ human insulin; Nle$^{42}$ human insulin; Thr$^{42}$ human insulin; Pro$^{42}$ human insulin; D-allo Ile$^{42}$ human insulin; Nva$^{43}$ human insulin; Leu$^{43}$ human insulin; Val$^{42}$, Ile$^{43}$ human insulin; Abu$^{42}$, Abu$^{43}$ human insulin; D-Cys$^{46}$ human insulin; D-Cys$^{46}$, C-Cys$^{411}$ human insulin; Ser$^{46}$, Ser$^{411}$, des (A8-A10) human insulin; D-Cys$^{47}$ human insulin; D-Cys$^{411}$ human insulin; Leu$^{419}$ human insulin; Gly$^{B6}$ human insulin; Glu$^{B12}$ human insulin; Asn$^{B12}$ human insulin; Phe$^{B12}$ human insulin; and D-Ala$^{B12}$ human insulin.

In certain embodiments of this invention, two, three, or a higher plurality of inducing antigens is used. It may be desirable to implement these embodiments when there are a plurality of target antigens, or to provide a plurality of bystanders for the target. For example, both insulin and glucagon can be mixed with a mucosal binding component in the treatment of diabetes. It may also be desirable to provide a cocktail of antigens to cover several possible alternative targets. For example, a cocktail of histocompatibility antigen fragments could be used to tolerize a subject in anticipation of future transplantation with an allograft of unknown phenotype. Allovariant regions of human leukocyte antigens are known in the art: e.g., *Immunogenetics* 29:231, 1989. In another example, a mixture of allergens may serve as inducing antigen for the treatment of atopy.

Inducing antigens can be prepared by a number of techniques known in the art, depending on the nature of the molecule. Polynucleotide, polypeptide, and carbohydrate antigens can be isolated from cells of the species to be treated in which they are enriched. Short peptides are conveniently prepared by amino acid synthesis. Longer proteins of known sequence can be prepared by synthesizing an encoding sequence or PCR-amplifying an encoding sequence from a natural source or vector, and then expressing the encoding sequence in a suitable bacterial or eukaryotic host cell.

In certain embodiments of this invention, the combination comprises a complex mixture of antigens obtained from a cell or tissue, one or more of which plays the role of inducing antigen. The antigens may be in the form of whole cells, either intact or treated with a fixative such as formaldehyde, glutaraldehyde, or alcohol. The antigens may be in the form of a cell lysate, created by detergent solubilization or mechanical rupture of cells or tissue, followed by clarification. The antigens may also be obtained by subcellular fractionation, particularly an enrichment of plasma membrane by techniques such as differential centrifugation, optionally followed by detergent solubilization and dialysis. Other separation techniques are also suitable, such as affinity or ion exchange chromatography of solubilized membrane proteins.

Antigens may also be in the form of food products which are eaten and the antigens released into the mucosa during digestion. Such food products include those containing grains, seeds or nuts or related products such as oils; milk or milk solids; cheeses; fruits; vegetables; seafood; spices and eggs or related products such as egg whites and albumin. Also included are food products containing small molecule compounds that are a target for hypersensitivity—for example, dyes such as FD&C Yellows 5 & 6, and preservatives, byproducts and flavor enhancers such as sulfates and monosodium glutamate. Antigens may also be expressed or present in the individual in response to or in association with a pathological condition, such as those associated with mucosal disorders. Exemplary mucosal disorders include inflammatory bowel disease, irritable bowel syndrome, ulcerative colitis, Celiac disease and Crohn's disease.

Mixtures of antigens from cells or tissues are of particular interest in a number of applications of this invention. For example: (1) For the treatment of organ-specific autoimmune disease, where the identity of the target antigen or a suitable bystander antigen is unknown, or to provide a plurality of antigens to heighten the tolerogenic response. Suitable sources of cells for this purpose would be a biopsy sample of the same tissue from the subject to be treated, or a cultured cell line of the same tissue type. (2) To tolerize a recipient to a planned tissue graft. Where the phenotype of the donor is known at the time of tolerization, the cell source is preferably obtained from either the donor or an individual sharing at least one major histocompatibility complex allotype with the donor. In humans, preferably two or more allotypes are shared at the HLA-A/B and HLA-DR locus (in order of increasing preference in the treatment of graft rejection; in the order of decreasing preference in the treatment of graft-versus-host disease). For tolerization against histocompatibility class II antigens (the usual target of an acute allograft rejection), peripheral blood mononuclear cells, spleen cells or lymph node cells are particularly appropriate. For tolerization against carbohydrate antigens (the usual target of hyperacute xenograft rejection), it is appropriate to use any cell type that is enriched at the target, such as endothelial cells or leukocytes. Where the phenotype of the donor is unknown at the time of tolerization, it is suitable to use a mixture of cells (such as mononuclear leukocytes) taken from several members of an out-bred population of the same species.

Assembly and Testing of the Combination

The combinations of this invention are assembled by combining one or more inducing antigens with one or more mucosal binding components. This is most conveniently performed in a relatively neutral aqueous solvent or buffer such as water, isotonic saline, phosphate buffer, or bicarbonate, or any pharmacologically and physiologically compatible excipient. Where the combination is to be stored or administered in solid form, the components may be combined as solids, permitting the mixture to form upon resuspension or dissolution.

The inducing antigen(s) and mucosal binding component(s) are combined at the ratio of an effective combination. Generally, an effective combination will be between about 100:1 and about 1:100 by weight; usually it will be between about 20:1 and about 1:20 by weight; and typically it will be between about 5:1 and about 1:5 by weight. A good starting point for the testing of new combinations is a weight ratio of about 1:1. After combining, the mixture is divided, if necessary, so that each division contains the amount of antigen desired for a single administration.

Combinations can be tested for their ability to promote tolerance by conducting experiments with isolated cells or in animal models.

A proxy for tolerogenic activity is the ability of an intact antigen or fragment to stimulate the production of an appropriate cytokine at the target site. The immunoregulatory cytokine released by T suppressor cells at the target site is thought to be TGF-β (Miller et al., *Proc. Natl. Acad. Sci. USA* 89:421, 1992). Other factors that may be produced during tolerance are the cytokines IL4 and IL-10, and the mediator PGE. In contrast, lymphocytes in tissues undergoing active immune destruction secrete cytokines such as IL-1, IL-2, IL-6, and γ-IFN. Hence, the efficacy of a candidate inducing antigen can be evaluated by measuring its ability to stimulate the appropriate type of cytokines.

With this in mind, a rapid screening test for tolerogenic epitopes of the inducing antigen, effective mucosal binding components, effective combinations, or effective modes and schedules of mucosal administration can be conducted using syngeneic animals as donors for in vitro cell assays. Animals are treated at a mucosal surface with the test composition, and at some time are challenged with parenteral administration of the target antigen in complete Freund's adjuvant. Spleen cells are isolated, and cultured in vitro in the presence of the target antigen at a concentration of about 50 μg/mL. Target antigen can be substituted with candidate proteins or sub-fragments to map the location of tolerogenic epitopes. Cytokine secretion into the medium can be quantitated by standard immunoassay.

The ability of the cells to suppress the activity of other cells can be determined using cells isolated from an animal immunized with the target antigen, or by creating a cell line responsive to the target antigen (Ben-Nun et al., *Eur. J. Immunol.* 11:195, 1981). In one variation of this experiment, the suppressor cell population is mildly irradiated (about 1000 to 1250 rads) to prevent proliferation, the suppressors are co-cultured with the responder cells, and then tritiated thymidine incorporation (or MTT) is used to quantitate the proliferative activity of the responders. In another variation, the suppressor cell population and the responder cell population are cultured in the upper and lower levels of a dual chamber transwell culture system (Costar, Cambridge Mass.), which permits the populations to coincubate within 1 mm of each other, separated by a polycarbonate membrane (WO 93/16724). In this approach, irradiation of the suppressor cell population is unnecessary, since the proliferative activity of the responders can be measured separately.

In embodiments of the invention where the target antigen is already present in the individual, there is no need to isolate the antigen or precombine it with the mucosal binding component. For example, the antigen may be expressed in the individual in a certain fashion as a result of a pathological condition (such as inflammatory bowel disease or Celiac disease) or through digestion of a food allergen. Testing is performed by giving the mucosal binding component in one or more doses or formulations, and determining its ability to promote tolerization against the antigen in situ.

The effectiveness of compositions and modes of administration for treatment of specific disease can also be elaborated in a corresponding animal disease model. The ability of the treatment to diminish or delay the symptomatology of the disease is monitored at the level of circulating biochemical and immunological hallmarks of the disease, immunohistology of the affected tissue, and gross clinical features as appropriate for the model being employed. Non-limiting examples of animal models that can be used for testing are included in the following section.

Specific Tolerization for Purposes of Treatment

The compositions and methods of this invention can be brought to bear whenever it is desirable to forestall or suppress an unwanted immunological response. This is appropriate in the treatment of a number of human and veterinary conditions.

Treatment is performed by administering an effective combination of mucosal binding components and antigen at an effective amount. A pharmaceutical composition or treatment protocol is effective if it results in a beneficial or desired clinical result, after one or more administrations.

Certain embodiments of this invention relate to priming of immune tolerance in an individual not previously tolerized by therapeutic intervention. These embodiments generally involve a plurality of administrations of a combination of antigen and mucosal binding component. Typically, at least three administrations, frequently at least four administrations, and sometimes at least six administrations are performed during priming in order to achieve a long-lasting result, although the subject may show manifestations of tolerance early in the course of treatment. Most often, each dose is given as a bolus administration, but sustained formulations capable of mucosal release are also suitable. Where multiple administrations are performed, the time between administrations is generally between 1 day and 3 weeks, and typically between about 3 days and 2 weeks. Generally, the same antigen and mucosal binding component are present at the same concentration, and the administration is given to the same mucosal surface, but variations of any of these variables during a course of treatment may be accommodated.

Other embodiments of this invention relate to boosting or extending the persistence of a previously established immune tolerance. These embodiments generally involve one administration or a short course of treatment at a time when the established tolerance is declining or at risk of declining. Boosting is generally performed 1 month to 1 year, and typically 2 to 6 months after priming or a previous boost. This invention also includes embodiments that involve regular maintenance of tolerance on a schedule of administrations that occur semiweekly, weekly, biweekly, or on any other regular schedule.

This invention contemplates treatment combinations in which embodiments described herein are used simultaneously or sequentially with other modes of inducing tolerance or otherwise treating the clinical condition. This includes but is not limited to mucosal administration of antigen alone, mucosal binding component alone, or covalent conjugates of antigen and mucosal binding component; or intravenous administration of tolerogenic substances of any kind.

Treatment is generally more effective in preventing the most severe consequences of an immune-mediated disease when performed on a prophylactic basis. There are several reasons for this. First, tolerization may be more effective in limiting the onset of an unwanted immunological reaction than in reversing it. Second, an unwanted immunological reaction may irreversibly damage a target organ or tissue. For example, insulin-secreting beta cells of the pancreas are eliminated in Type I diabetes. Accordingly, it is often appropriate to begin prophylactic administration to a subject identified at being at sufficient risk for the disease due to family history, biochemical, immunological, or genetic markers, or early clinical features.

Nevertheless, the practicing clinician will also recognize opportunities to use this invention in the treatment of active disease. Palliation of the condition is certainly a worthwhile outcome, even where complete reversal is not possible. Ongoing pathology attributable to an immunological reaction may benefit from tolerization—such as in systemic lupus, rheumatoid arthritis, or mucosal disorders such as inflammatory bowel disease, irritable bowel syndrome, Celiac disease, or Crohn's disease. Diabetes may be worth treating in the active state by invoking tolerance when beta-cell destruction is incomplete, where there is antibody that diminishes the effectiveness of insulin administered to regulate glucose metabolism, or where a beta-cell transplantation is planned. Other hypersensitivity responses, such as food allergies, can be provoked by a source of target antigen, for example, by eating foods known to stimulate such a response in the individual. Treatment according to this invention would include administration of the mucosal binding component to the sensitized mucosal surface at about the time when exposure is likely.

Illustration of Diseases Treatable by Specific Tolerization

The compositions and methods for inducing specific immunological tolerance disclosed herein can be brought to bear in the management of a number of different conditions. What follows are non-limiting illustrations of certain conditions of interest.

Certain embodiments of this invention relate to treatment of pathological conditions in which autoimmunity plays a part. Autoimmune diseases can be characterized as organ-specific and systemic. The pathology can include antibody-mediated or cell mediated cytolysis of the affected tissue, inflammatory destruction mediated by T helper/inducer cells, deposition of immune complexes, and antibody-mediated receptor triggering or blocking. Non-limiting examples of conditions that can be treated according to this invention include the following.

TABLE I

| Autoimmune Diseases | | |
|---|---|---|
| Condition | Target Tissue or Antigen | Additional Inducing or Bystander Antigen |
| Addison's disease; Adrenalitis | Adrenal cells | |
| Autoimmune hemolytic anemia | Red cell membrane proteins | |
| Chronic active hepatitis | Liver cell antigens | |

TABLE I-continued

| Autoimmune Diseases | | |
|---|---|---|
| Condition | Target Tissue or Antigen | Additional Inducing or Bystander Antigen |
| Goodpasture's syndrome | Renal and lung basement membranes | |
| Grave's disease | TSH receptor | |
| Hashimoto's thyroiditis | Thyroid cell antigens | Thyroglobulin |
| Idiopathic thrombocytopenia purpura | Platelet membrane proteins | |
| Insulin-dependent (Type I) diabetes mellitus | Pancreatic beta cell antigen | Insulin, glucagon, amylin, gamma amino decarboxylase, heat shock protein |
| Multiple sclerosis | Myelin sheath of central nervous system white matter | Myelin basic protein (MBP), PLP |
| Myasthenia gravis | Acetyl choline receptors | |
| Myocardial infraction; Rheumatic carditis | Heart antigens | |
| Pernicious anemia | Gastric parietal cells Intrinsic Factor | |
| Polymyositis | Muscle cell antigen | |
| Rheumatoid arthritis | Connective tissue | Collagen* (especially types II, IX, and XI), heat shock protein |
| Scleroderma | (Nuclei, heart, lungs, gastrointestinal tract, kidney) | Skin cell extract |
| Sjogren's syndrome | (Salivary gland, liver, kidney, thyroid) | |
| Spontaneous infertility | Sperm antigens | |
| Systemic lupus erythematosis | DNA, nuclear protein, red cell and platelet membranes | |
| Uveitis | Ocular antigen | S-antigen, interphotoreceptor retinoid binding protein |

For collagen types suitable as inducing antigens for other clinical conditions, the reader is referred to International Patent Publication WO 96/21458.

A number of animal models for autoimmune conditions have been established in the art. For example, insulin-dependent diabetes (Martin et al., *J. Autoimmunity* 9:637, 1996; Yang et al., *Proc. Natl. Acad. Sci. USA* 90:10494, 1993; von Herrath et al., *J. Clin. Invest.* 98:1324, 1996; and Examples 1 and 3), arthritis (Zeidler et al., *Autoimmunity* 21:245, 1995; WO 96/21458; Pearson et al., *J. Chronic Dis.* 16:863, 1963; and Example 4), multiple sclerosis (Alvord et al., "Experimental Allergic Encephalomyelitis . . . ", Allan R. Liss NY, 1984; and Example 4), and autoimmune uveo-retinitis (WO 91/01333).

Other embodiments of this invention relate to treatment of pathological conditions relating to an unwanted hypersensitivity. The hypersensitivity can be any one of types I, II, III, and IV. Immediate (type I) hypersensitivity is typically treated by using one or more offending allergen or tolerogenic fragments thereof as the inducing antigen. The frequency of administration will typically correspond with the timing of allergen exposure. Suitable animal models are known in the art (for example, Gundel et al., *Am. Rev. Respir. Dis.* 146:369, 1992; Wada et al., J. Med. Chem. 39, 2055, 1996; and WO 96/35418).

Other embodiments of this invention relate to transplantation. This refers to the transfer of a tissue sample or graft from a donor individual to a recipient individual, and is frequently performed on human recipients who need the tissue in order to restore a physiological function provided by the tissue. Tissues that are transplanted include (but are not limited to) whole organs such as kidney, liver, heart, lung; organ components such as skin grafts and the cornea of the eye; and cell suspensions such as bone marrow cells and cultures of cells selected and expanded from bone marrow or circulating blood, and whole blood transfusions.

A serious potential complication of any transplantation ensues from antigenic differences between the host recipient and the engrafted tissue. Depending on the nature and degree of the difference, there may be a risk of an immunological assault of the graft by the host, or of the host by the graft, or both, may occur. The extent of the risk is determined by following the response pattern in a population of similarly treated subjects with a similar phenotype, and correlating the various possible contributing factors according to well accepted clinical procedures. The immunological assault may be the result of a preexisting immunological response (such as preformed antibody), or one that is initiated about the time of transplantation (such as the generation of $T_H$ cells). Antibody, $T_H$ cells, or $T_C$ cells may be involved in any combination with each other and with various effector molecules and cells.

It is an object of this invention to provide materials and procedures that permit transplantation to be conducted according to standard surgical procedures, but with decreased risk of an adverse immunological reaction to the recipient of the transplant. The procedures involve tolerizing the recipient to the tissues of the donor, or vice versa, or both. The tolerizing is performed by administering a target antigen expressed in the transplanted tissue, or a bystander antigen, in an unconjugated combination with a mucosal binding protein. The ease of preparation of effective combination means that they can be prepared on little notice, tailor-made according to the phenotype of the donor and recipient. The graft may be a complex structure of many different cell types, and any one or more of the cell types transplanted into the individual may pose a risk for which the procedures of this invention are appropriate. For example, endothelial cell antigens complicate renal transplants, and passenger lymphocytes complicate hepatic transplants.

Certain embodiments of the invention relate to decreasing the risk of host versus graft disease, leading to rejection of the tissue graft by the recipient. The treatment may be performed to prevent or reduce the effect of a hyperacute, acute, or chronic rejection response. Treatment is preferentially initiated sufficiently far in advance of the transplant so that tolerance will be in place when the graft is installed; but where this is not possible, treatment can be initiated simultaneously with or following the transplant. Regardless of the time of initiation, treatment will generally continue at regular intervals for at least the first month following transplant. Follow-up doses may not be required if a sufficient accommodation of the graft occurs, but should be resumed if there is any evidence of rejection or inflammation of the graft. Of course, the tolerization procedures of this invention may be combined with other forms of immunosuppression to achieve an even lower level of risk.

In one example, xenotransplantation of porcine kidneys into other species is at risk of a hyperacute rejection due primarily but not exclusively to preformed antibody against the trisaccharideGalα1-3Galβ1-4GlcNAcβ1-, expressed on renal endothelial cells. Accordingly, in anticipation of a porcine allograft, the recipient may be tolerized in advance using a composition in which the trisaccharide is the inducing antigen. Alternatively, a pig endothelial cell extract may be used, to promote tolerization not only against the dominant trisaccharide, but against other trisaccharides, xenogeneic determinants on histocompatibility antigens, and unpredicted antigen mismatches. In a second example, an interhuman kidney allograft is at risk of an acute (primarily $T_H$ mediated) rejection response due to discordance of histocompatibility class II antigens. Accordingly, tolerization of the recipient before, during or after transplantation could be performed using isolated or recombinant human leukocyte antigen (HLA) class II of the donor's phenotype. Alternatively, cells or a cell extract from the donor could be used as the inducing antigen, to tolerize against both class II discordance and other mismatches. A preferred cell type for this application would preferably express class II antigens at substantial levels, particularly B cells, monocytes, and macrophages. These cells can be obtained from peripheral blood (if available), from lymph nodes, or from spleen. A mononuclear leukocyte population (obtained by centrifugation on a medium like Histopaque Ficoll™) will generally be well enriched in class II antigens. It is also possible to pre-tolerize a subject on a transplantation waiting list to a number of potential donors by giving a cocktail of recombinant HLA antigens, or an extract of a mixed leukocyte population from a number of different donors.

Certain embodiments of this invention relate to decreasing the risk of graft versus host disease. In this series of embodiments, it is necessary to tolerize a living donor against a target antigen of the future graft recipient before the transplantation occurs. Once tolerance is achieved, the cells or tissue of the donor are harvested and the transplant is performed.

In one example, a non-autologous bone-marrow donor is pre-tolerized to the tissues of recipient, preventing lymphocytes in the graft from generating a systemic graft-versus-host disease where the recipient is immunocompromised. Since the graft-versus-host disease is typically directed to human leukocyte antigens, a suitable inducing antigen for the composition given to the donor is isolated or recombinant HLA of the recipient's phenotype, or a leukocyte extract from the recipient. Applying most traditional non-specific forms of immunosuppression to the donor source would be incompatible with the objectives of transplant. The procedures of this invention are advantageous in that the induced tolerance is specific, and should not interfere with the function of the graft. In another example, the hemolytic activity due to passenger lymphocytes specific for blood group antigens in hepatic grafts is minimized by tolerizing the donor subject using antigens or red cells of the recipient's type.

Pharmaceutical Compositions and Their Administration

Compositions of this invention can be prepared for administration to an individual in need thereof, particularly human subjects having an unwanted immune response. The preparation of compositions and their use is conducted in accordance with generally accepted procedures for the preparation of pharmaceutical compositions.

In certain embodiments of this invention, the mucosal binding component and the antigen or antigen mixture are given together. The components are typically combined in an effective proportion within a single pharmaceutical composition, or by mixing just prior to administration. In other embodiments, the mucosal binding component is administered as a separate formulation from the antigen. For example, when the antigen is a food component, the mucosal binding component can be given with food, or during a period preceding or following food that would permit the mucosal binding component to promote tolerance to the component. The mucosal binding component and the inducing antigen are given as close together in time as practicable; preferably within less than about 6 hours, and more preferably within less than 30 min. In another example, an autoantigen already present in the mucosal surface is supplemented with a formulation containing the mucosal binding component.

Procedures for preparing pharmaceutical compositions are described in Remington's Pharmaceutical Sciences, E. W. Martin ed., Mack Publishing Co., Pa. The mucosal binding component and the antigen (whether given separately or together) are optionally combined with other active components, carriers and excipients, and stabilizers. Additional active components of interest are agents that enhance the tolerogenic effect of the combination at the mucosal surface. An example of an additional active component is a cytokine, exemplified by IL-4. Although not required, pharmaceutical compositions can be supplied in unit dosage form suitable for administration of a precise amount.

Certain embodiments of this invention relate to kits and reagents in which one or more component is provided in a separate container, optionally with written instructions, for assembly of a pharmaceutical composition by the patient or the administering health professional. In one example, an inducing antigen and a mucosal binding component are provided in separate containers of a kit to be combined just before administration. In a second example of interest for transplantation, a panel of possible inducing antigens (say, a panel of recombinant HLA antigens or leukocyte extracts of different donors) is provided along with a mucosal binding component, so that the administering professional can choose the appropriate inducing antigen for use in the composition. In a third example, a mucosal binding protein is provided by itself, optionally with other ingredients such as buffers and cofactors like IL-4, for purposes of combining with inducing antigen, particularly cells or a cell extract prepared near the time of administration by the professional.

Since the compositions are intended for mucosal administration, it is useful to prepare compositions that are not only stable for the expected shelf life, but also resistant to the pH extremes, enzymes, and other assaults of the mucosal environment. For example, binding agents that keep peptides together without impairing their ability to bind or penetrate the mucosal surface may be a helpful adjunct.

Insulin is stabilized by the presence of metal cations, particularly zinc. In neutral or moderately alkaline solutions (typical of the intestine), the predominant form of insulin is hexamer, with about 2 zinc ions per hexamer complex. It is mainly the non-polar residues of the insulin monomer involved in polymer association, leaving a surface that is almost entirely polar. Accordingly, the use of sufficient metal cations, particularly zinc, is recommended for compositions containing insulin. Many commercial insulin preparations come with a certain amount of zinc present, but others do not, and will need to be supplemented if its presence is desired. The amount required is 0.38 weight percent for 2 zinc ions per insulin hexamer, or 0.76 weight percent for 4 per hexamer.

Without intending to be limited by theory, one possible reason that the insulin containing zinc works better in certain embodiments than insulin without zinc is a bigger size of the zinc-containing insulin complex compared to the free insulin. It has been demonstrated (Frey et al. *J. Exp. Med.* 184:1045–1059, 1996) that small molecules primarily are targeted to intestinal epithelial cells and larger molecules to M-cells. M-cells are responsible for transport of protein to the Peyer's Patch for interaction with T-cells, which then enter the systemic circulation (Weiner et al., *Immunology Today,* 18:335–343, 1997). Regulatory T cells from Peyer's Patches may be responsible for conveying tolerance induced by this invention back to the target site. It can be theorized that zinc-containing complexes are more directly targeted to the M-cells because of their bigger size, which accounts for their effectiveness at inducing tolerance.

The exact nature of pharmaceutical compositions of this invention will often depend, in part, on the intended route of administration. Selection of a route of administration of a pharmaceutical composition to a mucosal surface will in turn depend, inter alia, on the clinical condition being treated, and the ease of administration to a particular surface. The most typical mucosal surfaces used are those of the gastrointestinal tract, the nasal mucosa, and the airway mucosa.

Administration to the gastrointestinal tract may be performed by oral administration, suppositories, intubation, endoscopy, or any other suitable technique. Compositions for oral administration are typically liquids, pills, or capsules. Liquid compositions can be supplied as liquid solutions or suspensions, or as solid forms suitable for dissolution or suspension in liquid prior to use.

Oral compositions containing insulin particularly benefit from the presence of sufficient amounts of zinc for hexamer formation. Liquid or easily soluble compositions may also subject insulin to the risk of degradation in the low pH of the stomach, and it may be beneficial to reduce this risk using bicarbonate or another accepted antacid preparation, either before or concurrently with the insulin, to raise the stomach pH above ~4. Other insulin compositions particularly suitable for oral administration are enteric coated pills, enclosed in gelatin capsules, or otherwise formulated so as to release their contents after passing through the stomach. Microparticle preparations such as liposomes and gellable hydrocolloids encapsulating the inducing antigen and the mucosal binding protein may also be effective (e.g., EP Patent Application 0635261 A1). Where the antigen of the composition is something other than insulin, the importance of protecting the antigen by one or more of these strategies will depend on its susceptibility to the gastrointestinal environment. For a general review for targeting drugs to the gut, see Wilding et al. (Pharmac. Ther. 62:97, 1994).

Nasal administration typically involves the use of a free-flowing liquid, cream or gel containing an effective concentration in a comfortable volume. Because the nasal mucosa is relatively more quiescent and there is a relative paucity of proteolytic enzymes, an effect may in some instances be obtained using a lower amount of antigen.

Administration to the mucosa of the airway typically involves the formation and inhalation of an aerosol. The aerosol may either be a finely dispersed liquid, or a powder. Apparatus and methods for forming aerosols are described in Kirk-Othmer, "Encyclopedia of Chemical Technology", 4th Ed Vol. 1, Wiley NY, pp 670–685, 1991; and Newman, "Aerosols and the Lung", Clarke & Davia, eds, Buttersworths, London Engl., pp 197–224, 1984. The reader may also consult U.S. Pat. Nos. 4,624,251; 3,703,173; 3,561,444; and 4,635,627. Portable inhalers permit dosages to be conveniently administered a number of times a day, where necessary.

The size of the dose is selected taking into account the expected volume of distribution of the composition before reaching the intended site of action, the degree of degradation and penetration expected for the mode of administration, the frequency of administration, and other relevant features such as the age and clinical condition of the subject being treated. Generally, a single administration for oral administration to a human subject will be between 10 μg and 50 mg of the antigen or antigen mixture, with a typical range being about 100 μg to 2 mg.

The assessment of the clinical features and the design of an appropriate therapeutic regimen for the individual patient is ultimately the responsibility of the prescribing physician.

The foregoing description provides, inter alia, a detailed explanation of how immunological tolerance can be induced in a subject, using effective combinations of components. It is understood that variations may be made with respect to both the nature of the compositions and their use without departing from the spirit of this invention.

All patents, patent applications, articles and publications mentioned herein, both supra and infra, are hereby incorporated herein by reference in their entirety.

The examples presented below are provided as a further guide to a practitioner of ordinary skill in the art, and are not meant to be limiting in any way.

EXAMPLES

Example 1

Treatment of NOD Mice for Symptoms of Diabetes Using a Non-covalent Mixture of Insulin and Cholera-toxin B This experiment was performed to characterize the ability of CTB mixed with insulin to induce immunological tolerance and prevent the symptoms of diabetes in a NOD mouse model. Insulin-dependent diabetes arises spontaneously in NOD mice, with a median time of about 20 weeks after birth.

Recombinant human insulin and purified pork insulin were obtained from Novo Nordisk, Bagsvaerd, Denmark. Both of these preparations are crystallized and contain zinc. Insulin precursor "M13", comprising the amino acid sequence AAK between the B chain and the A chain (but free of leader sequence), was obtained by recombinant expression of the precursor encoding region. The M13 preparation contained no zinc. Cholera toxin B subunit (CTB) was purified by a combination of hexametaphosphate precipitation and Sephadex™ G-75 gel filtration chromatography from culture filtrate of a mutant strain of *Vibrio cholerae* deleted of cholera toxin genes and complemented with a recombinant overexpression plasmid encoding CTB (Lebens et al., Bio/Technology 11:1574, 1993).

Insulin was dissolved in 0.35 M sodium bicarbonate to 20 mg/mL. CTB was dissolved in phosphate-buffered saline pH 7.4 (PBS), to 5 mg/mL. The solutions were mixed at an equal ratio by weight, and then diluted with PBS to give the desired amount in a 250 μL volume. Another 250 μL of bicarbonate was added to buffer stomach acid. Compositions were administered to female NOD mice by oral gavage through an 18-gauge stainless steel feeding needle.

Mice were divided into the groups shown in Table 2. Doses were given on a biweekly schedule at weeks 10, 12, 14, 16, 18, and 20 after birth.

TABLE 2

NOD mouse treatment groups

| Group | Oral Treatment (6 administrations each) | Number of mice |
|---|---|---|
| 1 | 10 μg human insulin + 10 μg CTB | 18 |
| 2 | 100 μg human insulin + 100 μg CTB | 18 |

TABLE 2-continued

NOD mouse treatment groups

| Group | Oral Treatment (6 administrations each) | Number of mice |
|---|---|---|
| 3 | 1000 μg human insulin + 1000 μg CTB | 18 |
| 4 | 100 μg M13 precursor + 100 μg CTB | 18 |
| 5 | 100 μg porcine insulin + 100 μg CTB | 18 |
| 6 | 100 μg human insulin (no Zn) + 100 μg CTB | 18 |
| 7 | 1000 μg CTB alone | 18 |
| 8 | 1000 μg human insulin alone | 18 |
| 9 | sham (buffer control) | 22 |

Animals were monitored weekly for signs of diabetes throughout treatment and in the ensuing weeks. An animal was considered diabetic if it had a positive urine glucose test (measured using urine chemistrips from Bayer, Germany), and random blood glucose levels persisting above 15 mM.

Results are shown in Table 3. All animals survived to the 27 week point and are counted in the data. Probability of significant difference from the sham-treated group was calculated using Fisher's Exact Test.

TABLE 3

Effect of Treatment

| Group | Prevalence (% mice that are diabetic) | | Significance |
|---|---|---|---|
| | Week 23 | Week 27 | Week 27 |
| 1 | 44% | 56% | .18 |
| 2 | 27% | 44% | .05 |
| 3 | 50% | 89% | 1.00 |
| 4 | 50% | 67% | .50 |
| 5 | 33% | 44% | .05 |
| 6 | 56% | 61% | .32 |
| 7 | 44% | 72% | .73 |
| 8 | 27% | 67% | .50 |
| 9 | 50% | 77% | — |

The results from the sham-treated group track the rate of progression of spontaneous diabetic symptoms in this strain. Significantly lower frequency of symptoms in a treatment group indicates that the treatment has delayed disease onset in a proportion of the animals in the group.

Three weeks after the last administration, the frequency of symptoms was lower in Groups 2 and 5, which were given 100 μg insulin in combination with 100 μg CTB. Recombinant human insulin and purified pork insulin were equally effective, providing the insulin preparation contained zinc. Group 8 also showed a lower frequency of symptoms after treatment with insulin alone, but at the much higher level of 1000 μg.

The combination of 100 μg zinc-free insulin and 100 μg CTB used in Group 6 was ineffective, consistent with a role for zinc in maintaining the potency of the combination. Zinc is believed to keep insulin assembled as a hexamer, which may protect it during passage into the gastrointestinal system, and/or facilitate better penetration of the mucosal surface or uptake by antigen presenting cells. The combination of 100 μg M13 insulin precursor and 100 μg CTB was ineffective, and also attributed to a lack of zinc (Group 4). The precursor is otherwise predicted to be effective. The mixture of insulin and CTB is ineffective when given at the higher dose of 1000 μg of insulin (Group 3).

Seven weeks after the final administration, the progression of diabetic symptoms was still significantly delayed in Groups 2 and 5, with the frequency of symptoms reduced to 44% compared to 77% in the controls. Group 8 no longer was significantly different from controls. This indicates that 1000 μg insulin alone only temporarily delays symptoms. However, 100 μg insulin in combination with 100 μg CTB results in sustained immunological tolerance that delays the onset of symptoms in a significant proportion of animals for at least 7 weeks beyond the termination of treatment. The ratio of affected animals in treated versus control groups (44%/77%) indicates that the treatment was efficacious in about 43% of animals that would otherwise have developed symptoms by the 27 week point.

Example 2

Immunostimulatory Effects of Cholera Toxin B In Vitro

This example shows that CTB induces cytokine secretion by antigen-specific lymphocytes and promotes antigen presentation in culture.

10-week old BALB/c mice were immunized subcutaneously with 200 μg KLH (in PBS at 2 mg/mL) in complete Freund's adjuvant (0.4 mL final volume). Two weeks later, spleen cells were prepared and plated at $5 \times 10^5$ cells/well. The cells were incubated with a stimulatory agent, and the plates were developed according to the following assay.

Each well of a MultiScreen™ plate (Millipore Cat. MAIPS4510) is coated with 100 μL of 5 μg/mL cytokine antibody (anti IL-2, anti IL-4 or anti IFN-γ) overnight at 4° C. The plates are blocked with PBS containing 1% bovine albumin and 0.1% Tween™ 20 for 1 h at 37° C. The plates are washed in RPMI 1640 containing 10% fetal calf serum, and the splenocyte incubates at 37° C. and 5% $CO_2$ for 16–24 h. After 10 washings, 100 μL well of biotinylated anti-cytokine antibody (Pharmingen) is added at 2 μg/mL, and incubated for 2 h at 37° C. The plates are washed again, and horse radish peroxidase-conjugated anti-immunoglobulin at 2 μg/mL is incubated in the wells for 2 h at room temp. After washing, the chromogen substrate is added to develop the reaction according to manufacturer's directions (Vector AEC substrate kit for HRP, Cat. SK-4200). After washing and drying, the spots are counted under a microscope.

The results are shown in the following table:

TABLE 4

Effect of cholera toxin B lymphocyte cytokine expression

| Cytokine | KLH (10 μg/mL) | KLH (10 μg/mL) + CTB (5 μg/mL) | Medium + CTB (5 μg/mL) |
| --- | --- | --- | --- |
| IL-2 | 53 ± 14 | >300* | 2 ± 1 |
| IL-4 | 46 ± 13 | >300* | 2 ± 1 |
| IFN-γ | 5 ± 6 | 52 ± 7 | 2 ± 1 |

*limit of spots countable in one well

This shows that the addition of CTB enhances antigen-specific T-cell in vitro response by 5–10 fold, depending on the cytokine used for read-out. Since CTB did not stimulate splenocytes in the absence of KLH, it can be concluded that the stimulatory effect is antigen specific.

In a separate experiment, the effect of CTB on antigen-presenting cells was characterized. Splenocytes from 10-week-old BALB/c mice were preincubated with CTB (5 μg/mL) for 20 min at 37° C. The unbound CTB was washed away, and the treated cells were mixed at a ratio of 1:1 with $2.5 \times 10^5$ splenocytes from the KLH immunized animals, and then stimulated with or without KLH as described above.

The results were as follows:

TABLE 5

Effect of cholera toxin B on antigen presentation

| Cytokine | KLH (10 μg/mL) | KLH (10 μg/mL) + CTB (5 μg/mL) | Medium + CTB (5 μg/mL) |
| --- | --- | --- | --- |
| IL-4 | 39 ± 5 | 254 ± 9 | 5 ± 4 |
| IL-4 preincubated with CTB | 212 ± 8 | 263 ± 5 | 6 ± 3 |

The antigen specific response against KLH was enhanced by approximately 5-fold, as measured by an increase in IL-4 production. There was no effect on a mitogen-induced response (Con A), or non responding cells (medium control). This supports an immunostimulatory effect of CTB via enhanced antigen presentation. A 1–2 day incubation of CTB with the mouse antigen presenting cell line RAW 264 resulted in up-regulation of the following costimulatory molecules: B7-1, B7-2, VCAM, Class II MHC antigen, and MAC-1.

Example 3

Treatment in a Viral Induction Model of Type I Diabetes

The etiology of insulin-dependent (Type I) diabetes mellitus in humans is thought typically to involve a genetic predisposition to tissue-specific autoimmune disease, and a triggering event that initiates beta cell destruction. The triggering event may be infection by a foreign etiologic agent, such as a virus that mimics a component of the host expressed by beta cells.

Another animal model of interest is the transgenic mouse model of von Herrath et al. (*J. Clin. Invest.* 98:1324, 1996). The mice express the viral nucleoprotein of lymphocytic choriomeningitis virus (LCMV) under control of the rat insulin promotor in their beta cells. Less than 2% of the transgenic mice spontaneously develop diabetic symptoms, but two months after challenge with LCMV, the response frequency is >95%. Oral treatment with 1 mg insulin twice weekly for 2 months prevents diabetes in >50% of the mice when challenged with LCMV mid-course in the therapy.

In the experiment of this example, the transgenic mice are treated with combinations of this invention, challenged with LCMV to trigger the development of diabetes, and then monitored for symptoms for up to 2 months. Mixtures and administration is performed as in Example 1, using compositions comprising 100 μg human insulin containing zinc mixed with 100 μg CTB per administration. The gavage is performed twice weekly for 2 weeks either before or after the LCMV challenge, or both. Mice are defined as diabetic by random glucose determinations of >350 mg/mL in two consecutive measurements. The effect is compared between groups treated with the mixture, and groups treated with insulin alone or buffer control.

Example 4

Antigen-CTB Mixtures for Treatment of Other Immunologically Mediated Conditions

Compositions of this invention are tested in animal models for other diseases involving an unwanted immune response.

Multiple sclerosis is modeled by inducing experimental autoimmune encephalomyelitis (EAE) in 7–8 week old female Lewis rats. The animals are injected in the hind footpad with 50 μg Guinea pig myelin basic protein (MBP) in complete Freund's adjuvant. Tolerance is induced by gastric intubation of a mixture of 100 μg MBP and 100 μg CTB. Animals are fed the tolerogen either 1, 3 or 6 times either before or after induction of EAE, with either 2 or 5 day intervals between administrations.

Animals are examined daily for clinical signs of EAE according to the following scale: 0—no detectable disease; 1—limp tail; 2—tail paralysis and limb weakness; 3—hind limb paralysis; 4—tetraplegia; 5—death. The effect of MBP-CTB mixtures is compared with the effect of MBP alone and between different treatment schedules.

Arthritis is modeled by priming 8–14 week old DBA/1 Lac J mice with an intradermal injection of 300 μg type II collagen (Sigma) in complete Freund's adjuvant, followed 21 d later by a boosting dose of 100 μg type II collagen. Tolerance is induced by gastric intubation of a mixture of 10 or 100 μg type II collagen and an equal weigh of CTB. Animals are fed the tolerogen either 1, 3 or 6 times either before or after induction of arthritis, with either 2 or 5 day intervals between administrations.

The mice are examined 2–3 times per week for distal joint swelling and erythema (foot thickness and ankle width, measured using a constant tension caliper). A mouse is considered arthritic when swelling and erythema are observed by a substantial change in consecutive measurements in at least one paw. The following grading scale is used: 0—no detectable arthritis; 1—mild swelling and erythema; 2—swelling and erythema of both tarsus and ankle; 3—ankylosis and boney deformity. The effect of MBP-CTB mixtures is compared with the effect of MBP alone and between different treatment schedules.

Example 5

Tolerance Induction to Tetanus Toxin by Nasal or Oral Administration

In this experiment, tetanus toxin was tested as an alternative target antigen, and comparisons were made between gastrointestinal and nasal administration.

The protocol for this experiment was as follows. Whole tetanus toxin (TT) was obtained from Connaught Laboratories, Toronto Canada. Balb/c mice (female, 7–8 weeks old) were fed as indicated below and immunized with complete Freund's adjuvant in the foot pad mixed 1:1 with 50 μg tetanus toxin (TT) in PBS (final volume 10 μl). After 10 days, the draining lymph nodes were removed and made into a single cell suspension. They were stimulated in a 96 well plate with 100 μg/mL of tetanus toxin for 50 h (200,000 cells/200 μl in RPMI 1640 containing 5% fetal calf serum, 100 U/mL penicillin, 100 g/mL streptomycin and 2 mM glutamine) and then pulsed with 1 μCi methyl $^3$H-thymidine for 24 h. The cells were harvested and thymidine incorporation measured by scintillation counting. The stimulation index (S.I.) was calculated as T-cells in medium without antigens divided by T-cells stimulated with antigen. For oral feeding, the antigens were diluted in 0.35 M NaHCO$_3$ and a final volume of 0.5 mL was fed. For nasal administration, the antigens were diluted in PBS and a final volume of 0.01 mL was administered.

The treatment groups are shown in the following table.

TABLE 6

Treatment groups

| Group | Treatment | Number of mice |
|---|---|---|
| 1 | 100 μg TT + 100 μg CTB oral at day 0, day 7 and day 14 | 7 |
| 2 | 10 μg TT + 10 μg CTB oral at day 0, day 7 and day 14 | 6 |
| 3 | 100 μg TT oral at day 0, day 7 and day 14 | 6 |
| 4 | 100 μg CTB oral at day 0, day 7 and day 14 | 6 |
| 5 | 5000 μg TT oral at day 0, day 7 and day 14 | 6 |
| 6 | Control group: 0.35 M NaHCO$_3$ oral and PBS nasal without antigens day 0, day 7 and day 14 | 10 |
| 7 | 10 μg TT nasal at day 0, day 7 and day 14 | 6 |
| 8 | 10 μg TT + 10 μg CTB nasal at day 0, day 7 and day 14 | 6 |

Results are shown in the table below. Both oral and nasal administration of TT inhibited the response (group 3 and 7). However, by admixing TT with CTB, the effect was potentiated approximately 10 fold by oral delivery since oral feeding with 10 μg TT+10 μg CTB inhibit the T-cell proliferation as much as 100 μg of the tetanus toxin alone, 6.0 SI vs. 6.1 SI respectively, 100 μg TT+100 μg CTB oral further enhanced the inhibition, i.e. 4.5 S.I. Nasal administration was also effective in inhibiting T-cell proliferation. Comparing 10 μg TT alone with 10 μg TT+10 μg CTB, the best effect on T-cell proliferation inhibition was obtained with the admixture preparation, 4.9 SI vs. 4.4 SI respectively. Overall, the strongest effect on inhibiting T-cell proliferation was obtained with the nasal administration of 10 μg TT+10 μg CTB nasal, compared with either 10 μg TT nasal, 10 μg TT+10 μg CTB oral, 100 μg TT+oral or 5000 μg TT oral.

TABLE 7

In vitro stimutation of lymphocytes from treated mice using 100 μg/mL Tetanus Toxin

| Group | Stimulation Index | Standard Deviation |
|---|---|---|
| 1 | 4.5 | 0.5 |
| 2 | 6.0 | 0.4 |
| 3 | 6.1 | 0.7 |
| 4 | 9.2 | 0.4 |
| 5 | 5.4 | 0.7 |
| 6 | 9.3 | 1.2 |
| 7 | 4.9 | 0.4 |
| 8 | 4.4 | 0.3 |

It was concluded that the TT admixture potentiates oral tolerance approximately 10 fold, compared with using TT alone. Furthermore, nasal administration potentiates the effect on inhibiting T-cell proliferation approximately 10 fold when compared with oral administration, i.e. 10 μg TT+10 μg CTB nasal, works as well as 100 μg TT and 100 μg CTB oral, 4.4 SI vs 4.5 SI, respectively.

What is claimed as the invention is:

1. A method of inducing specific sustained immunological tolerance in an individual to a target antigen, comprising administering to a mucosal surface of the individual a composition comprising an effective combination of an inducing agent and a mucosal binding component selected from the group consisting of a cholera toxin B peptide (CTB) or an E. coli heat-labile enterotoxin B subunit (LTB) peptide in an unconjugated form, wherein the inducing agent is the target antigen.

2. The method of claim 1, wherein the mucosal binding component has GM1 binding activity.

3. The method of claim 1, wherein the mucosal binding component is a cholera toxin B peptide.

4. The method of claim 1, wherein the mucosal surface is the gastrointestinal mucosa and the composition is administered orally.

5. The method of claim 1, wherein the mucosal surface is the nasal mucosa and the composition is administered nasally.

6. The method of claim 1, wherein the mucosal surface is the airway mucosa and the composition is administered by aerosol.

7. The method of claim 1, comprising administering the composition to the mucosal surface on at least three successive occasions.

8. The method of claim 1, wherein the sustained immune tolerance persists for at least 5 weeks.

9. A method of inducing specific sustained immunological tolerance in an individual to an allergen or a mucosal antigen, comprising administering to a mucosal surface of the individual a composition comprising an effective combination of an inducing agent and an effective amount of a mucosal binding component selected from the group consisting of a cholera toxin B peptide (CTB) or an *E. coli* heat-labile enterotoxin B subunit (LTB) peptide in an unconjugated form, wherein the inducing agent is the allergen or the mucosal antigen.

10. The method according to claim 9, wherein immunological tolerance is induced against an allergen, and the administering of the mucosal binding component to the mucosal surface is performed during exposure of the same mucosal surface to the allergen.

11. The method according to claim 9, wherein immunological tolerance is induced against a mucosal antigen associated with an autoin-imune disease of the gastrointestinal tract, and the mucosal binding component is administered to the gastrointestinal tract.

12. A method for treating an autoimmune condition in an individual, comprising inducing specific sustained immunological tolerance according to the method of claim 1.

13. The method of claim 12 wherein the autoimmune condition is rheumatoid arthritis and the inducing antigen is a type II collagen peptide.

14. The method of claim 12, wherein the autoimmune condition is multiple sclerosis and the inducing antigen is a myelin basic protein peptide.

15. The method of claim 12, wherein the autoimmune condition is Type I diabetes and the inducing antigen is an insulin peptide.

16. A method of decreasing the risk of rejection in a recipient of a tissue graft transplanted from a donor, comprising inducing specific sustained immunological tolerance in the recipient to cells of the donor according to the method of claim 1 by administering to a mucosal surface of the recipient a composition comprising an effective combination of an inducing antigen and a mucosal binding component selected from the group consisting of a cholera toxin B peptide (CTB) or an *E. coli* heat-labile enterotoxin B subunit (LTB) peptide in an unconjugated form, wherein the inducing agent is the cells of the donor.

17. A method of decreasing the risk of graft-versus-host disease in a recipient from a tissue graft transplanted from a donor, comprising inducing specific sustained immunological tolerance in the donor to cells of the recipient according to the method of claim 1 by administering to a mucosal surface of the donor a composition comprising an effective combination of an inducing antigen and a mucosal binding component selected from the group consisting of a cholera toxin B peptide (CTB) or an *E. coli* heat-labile enterotoxin B subunit (LTB) peptide in an unconjugated form, wherein the inducing agent is the cells of the recipient.

* * * * *